United States Patent
Sano

(10) Patent No.: US 10,294,197 B2
(45) Date of Patent: May 21, 2019

(54) PURIFYING METHOD, PRODUCTION METHOD, AND DISTILLATION APPARATUS FOR ACRYLONITRILE

(71) Applicant: ASAHI KASEI KABUSHIKI KAISHA, Tokyo (JP)

(72) Inventor: Kazuhiko Sano, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/756,617

(22) PCT Filed: Aug. 21, 2017

(86) PCT No.: PCT/JP2017/029739
§ 371 (c)(1),
(2) Date: Mar. 1, 2018

(87) PCT Pub. No.: WO2018/074046
PCT Pub. Date: Apr. 26, 2018

(65) Prior Publication Data
US 2019/0047945 A1    Feb. 14, 2019

(30) Foreign Application Priority Data

Oct. 21, 2016   (JP) .................. 2016-207039

(51) Int. Cl.
| | |
|---|---|
| *C07C 253/34* | (2006.01) |
| *B01D 3/14* | (2006.01) |
| *B01D 3/40* | (2006.01) |
| *B01D 3/42* | (2006.01) |
| *C07C 253/26* | (2006.01) |
| *C07C 255/08* | (2006.01) |

(52) U.S. Cl.
CPC .............. *C07C 253/34* (2013.01); *B01D 3/14* (2013.01); *B01D 3/40* (2013.01); *B01D 3/42* (2013.01); *B01D 3/4261* (2013.01); *C07C 253/26* (2013.01); *C07C 255/08* (2013.01)

(58) Field of Classification Search
None
See application file for complete search history.

(56) References Cited

U.S. PATENT DOCUMENTS 6,107,509 A    8/2000    Hagans et al.

FOREIGN PATENT DOCUMENTS

| CN | 1345306 A | 4/2002 |
|---|---|---|
| JP | 61-180755 A | 8/1986 |
| JP | 2005-239574 A | 9/2005 |
| JP | 2007-39403 A | 2/2007 |
| JP | 2012-136483 A | 7/2012 |
| WO | WO 2012/090690 A1 | 7/2012 |
| WO | WO 2012/090691 A1 | 7/2012 |

OTHER PUBLICATIONS

International Search Report and Written Opinion of the International Searching Authority (forms PCT/ISA/210 and PCT/ISA/237), dated Oct. 24, 2017, for International Application No. PCT/JP2017/029739, with an English translation of the International Search Report.

*Primary Examiner* — Kamal A Saeed
(74) *Attorney, Agent, or Firm* — Birch, Stewart, Kolasch & Birch, LLP

(57) ABSTRACT

A method for purifying acrylonitrile involving a purification step of distilling an acrylonitrile solution containing acrylonitrile, hydrogen cyanide, and water, wherein the purification step involves a first step of separating a side stream withdrawn from a first position of a distillation column into an organic layer and an aqueous layer, and then returning the organic layer to a second position of the distillation column, the second position being positioned below the first position and a second step of supplying water from a third position of the distillation column, the third position being positioned below the second position and above a lowermost stage of the distillation column is a novel method in which stabilization of product quality and reduction in load on the acrylonitrile production process can be achieved by stabilizing a hydrocyanic acid-removing dehydration column in the process for producing acrylonitrile.

3 Claims, 2 Drawing Sheets

[Figure 1]
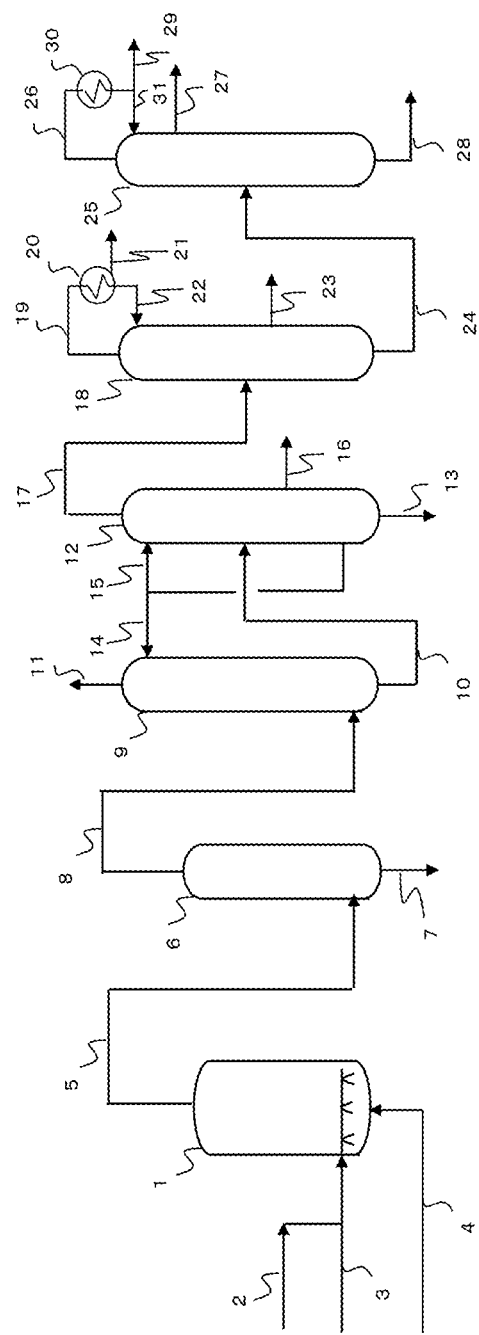

[Figure 2]
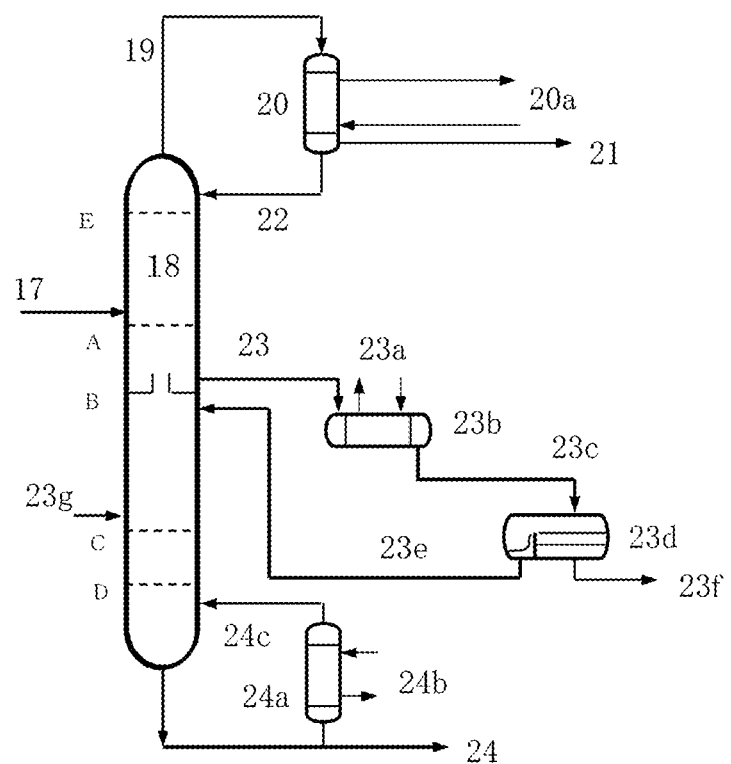

PURIFYING METHOD, PRODUCTION METHOD, AND DISTILLATION APPARATUS FOR ACRYLONITRILE

TECHNICAL FIELD

The present invention relates to a purifying method, a production method, and a distillation apparatus for acrylonitrile.

BACKGROUND ART

In a typical process of producing acrylonitrile by reacting: propylene and/or propane; ammonia; and oxygen in the presence of a catalyst, firstly, a reaction-generated gas containing generated acrylonitrile, acetonitrile, and hydrogen cyanide is cooled in a quench column, and unreacted ammonia is removed by neutralization with sulfuric acid. Thereafter, the reaction-generated gas is fed to an absorption column to allow acrylonitrile, acetonitrile, and hydrogen cyanide to be absorbed in water. Subsequently, an aqueous solution obtained in the absorption column and containing acrylonitrile and the like is introduced in a collection column, and the aqueous solution is separated into a fraction containing acetonitrile and most of water and a fraction containing most of acrylonitrile and hydrogen cyanide by distillation operation. Thereafter, the fraction containing most of acrylonitrile and hydrogen cyanide is introduced to a hydrocyanic acid-removing dehydration column to separate hydrogen cyanide and water from the fraction, and the bottom liquid is then introduced to a product column to purify acrylonitrile by distillation operation, thereby obtaining a product that conforms to a product specification.

Patent Literature 1 discloses a method for suppressing polymerization of acrylonitrile and hydrogen cyanide in purification of acrylonitrile by adding an acid and hydroquinone in the hydrocyanic acid-removing dehydration column.

CITATION LIST

Patent Literature

Patent Literature 1: Japanese Unexamined Patent Application Publication No. 2007-39403

SUMMARY OF INVENTION

Technical Problem

Conventionally, increasing the yield of acrylonitrile as a product has naturally been attracting much attention and has been studied. In the process for producing acrylonitrile, establishment of a technique on prevention of occurrence of clogging in the hydrocyanic acid-removing dehydration column due to polymer generation is a major problem. Stable operation of the hydrocyanic acid-removing dehydration column has major technical and economical merits of increasing the yield of acrylonitrile and stabilizing the product quality, in addition to stabilizing production steps; however, the present situation is that detailed studies have not been conducted so far.

In consideration of the circumstances, an object of the present invention is to provide a method that enables to achieve the stabilization of the process for producing acrylonitrile, the increase in the yield of acrylonitrile, and the stabilization of the product quality by making the operation of the hydrocyanic acid-removing dehydration column operable stably over a long period of time in the process for producing acrylonitrile.

Solution to Problem

The present inventor has conducted diligent studies to find that, in the purifying method comprising a step of distilling a solution containing acrylonitrile, hydrogen cyanide, and water in the process for producing acrylonitrile, when water is supplied to a particular position of a distillation column, the process is stabilized, the yield of acrylonitrile is increased, and the product quality can be stabilized, thereby completed the present invention.

That is, the present invention is as follows.

[1]

A method for purifying acrylonitrile comprising a purification step of distilling an acrylonitrile solution comprising acrylonitrile, hydrogen cyanide, and water, wherein the purification step comprises:

a first step of separating a side stream withdrawn from a first position of a distillation column into an organic layer and an aqueous layer, and then returning the organic layer to a second position of the distillation column, the second position being positioned below the first position; and a second step of supplying water from a third position of the distillation column, the third position being positioned below the second position and above a lowermost stage of the distillation column.

[2]

A method for producing acrylonitrile comprising:

a reaction step of reacting: propylene and/or propane; ammonia; and oxygen in the presence of a catalyst;

an absorption step of allowing a gas comprising generated acrylonitrile, acetonitrile, and hydrogen cyanide to be absorbed in water, thereby obtaining an aqueous solution;

a collection step of distilling the aqueous solution to obtain an acrylonitrile solution comprising acrylonitrile, hydrogen cyanide, and water; and a purification step of separating hydrogen cyanide and water from the acrylonitrile solution to obtain acrylonitrile, wherein the method for purifying acrylonitrile according to [1] is used in the purification step.

[3]

A distillation apparatus comprising:

a distillation column;

a first line that takes out a side stream from a first position of the distillation column;

a cooler that cools the side stream;

a decanter that separates the side stream having passed through the cooler into an organic layer and an aqueous layer;

a second line that returns the organic layer to a second position of the distillation column, the second position being positioned below the first position; and a third line that introduces water from a third position of the distillation column, the third position being positioned below the second position and above a lowermost stage of the distillation column.

Advantageous Effects of Invention

According to the present invention, the production process is stabilized, the yield of acrylonitrile is increased, and a high-quality product can be obtained stably by preventing the clogging of the distillation column in the process for producing acrylonitrile.

BRIEF DESCRIPTION OF DRAWINGS

FIG. 1 shows a schematic diagram conceptually illustrating one example of an acrylonitrile production process.

FIG. 2 shows a schematic diagram conceptually illustrating one example of a distillation apparatus (hydrocyanic acid-removing dehydration column and facilities connected thereto) according to the present invention.

DESCRIPTION OF EMBODIMENTS

Hereinafter, an embodiment for carrying out the present invention (hereinafter, present embodiment) will be described in detail. It is to be noted that the present invention is not limited to the present embodiment and can be carried out by being modified variously within the scope thereof.

Hereinafter, the present embodiment will be described with reference to the accompanying drawings as necessary. It is to be noted that the same elements will be given the same reference signs in the accompanying drawings, and any repetitive description will be omitted. In addition, the positional relationships, such as up-and-down and left-to-right relationships, are based on those illustrated in the accompanying drawings unless otherwise noticed. Various dimensional ratios among apparatuses and members are not limited to those illustrated in the accompanying drawings.

Method for Purifying Acrylonitrile

A method for purifying acrylonitrile according to the present embodiment is a method for purifying acrylonitrile comprising a purification step of distilling an acrylonitrile solution comprising acrylonitrile, hydrogen cyanide, and water, wherein
 the purification step comprises:
 a first step of separating a side stream withdrawn from a first position of a distillation column into an organic layer and an aqueous layer, and then returning the organic layer to a second position of the distillation column, the second position being positioned below the first position; and
 a second step of supplying water from a third position of the distillation column, the third position being positioned below the second position and above a lowermost stage of the distillation column.

Method for Producing Acrylonitrile

A method for producing acrylonitrile (hereinafter, also referred to as "acrylonitrile production process") according to the present embodiment is a method for producing acrylonitrile comprising:
 a reaction step of reacting: propylene and/or propane; ammonia; and oxygen in the presence of a catalyst;
 an absorption step of allowing a gas comprising generated acrylonitrile, acetonitrile, and hydrogen cyanide to be absorbed in water, thereby obtaining an aqueous solution;
 a collection step of distilling the aqueous solution to obtain an acrylonitrile solution comprising acrylonitrile, hydrogen cyanide, and water; and
 a purification step of separating hydrogen cyanide and water from the acrylonitrile solution to obtain acrylonitrile, wherein the method for purifying acrylonitrile according to the present embodiment is used in the purification step.

The method for producing acrylonitrile according to the present embodiment may further comprise a quench step of cooling a reaction-generated gas generated in the reaction step after the reaction step and before the absorption step.

FIG. 1 shows a schematic diagram schematically illustrating one example of a typical acrylonitrile production process. It is to be noted that, in the outline of the acrylonitrile production process below, the "hydrocyanic acid-removing dehydration column" in FIG. 1 will be described as the "distillation column" in the present embodiment.

Reaction Step

In the acrylonitrile production process, firstly, gaseous propylene and/or propane are supplied from a line 2, ammonia is supplied from line 3, and oxygen (air is usually used) is supplied from line 4 to a fluidized bed reactor 1 in which a fluidized bed catalyst is packed, and propylene and/or propane are then subjected to ammoxidation reaction. A reaction-generated gas contains: acetonitrile and hydrogen cyanide which are byproducts; propylene and/or propane, ammonia, and oxygen which are unreacted; and nitrogen and the like in addition to acrylonitrile as a product.

Quench Step

The reaction-generated gas obtained is withdrawn with a line 5 and is introduced into a quench column 6. In the quench column 6, the reaction-generated gas and water are brought into a countercurrent contact to cool the reaction-generated gas, thereby removing a high-boiling point substance and the fluidized bed catalyst slightly contained in the reaction-generated gas. In addition, unreacted ammonia is removed by neutralization with sulfuric acid. These high-boiling point substance, fluidized bed catalyst, and ammonium sulfate generated by neutralizing unreacted ammonia with sulfuric acid are withdrawn from a line 7 at the bottom of the quench column 6.

Absorption Step

A cooled gas taken out from the upper part of the quench column 6 is introduced into an absorption column 9 with a line 8. Water withdrawn from a collection column 12 is supplied to the top of the absorption column 9 with a line 14 as absorption water to allow acrylonitrile, acetonitrile, and hydrogen cyanide in the cooled gas to be absorbed in water, thereby obtaining an aqueous solution as a bottom liquid. Propylene, propane, oxygen, nitrogen, carbon dioxide gas, carbon monoxide gas, and a slight amount of an organic substance and the like which have not been absorbed are withdrawn outside the process system with a line 11 at the top of the absorption column.

Collection Step

The bottom liquid in the absorption column 9 is supplied to the collection column 12 from a line 10. Extraction water is introduced into the top of the collection column 12 with a line 15 to extract and separate acetonitrile by extractive distillation. Acetonitrile is withdrawn outside the process system with a line 16 as a side stream. In addition, most of water is withdrawn outside the process system from a line 13 as a bottom liquid. Acrylonitrile, hydrogen cyanide, and water are distilled out from the top of the collection column with a line 17, condensed with a condenser not illustrated in Figures, and then separated into two layers of an organic layer and an aqueous layer in a decanter not illustrated in Figures. In the condenser not illustrated in Figures, an aqueous hydroquinone solution is sprayed so that the concentration of hydroquinone in a line 24 is in a range of 100 to 600 ppm by mass. The organic layer (acrylonitrile solution) containing acrylonitrile, hydrogen cyanide, and a small amount of water is supplied to a hydrocyanic acid-removing dehydration column 18 from the line 17. The aqueous layer is joined in the line 10 to be recycled for the prior step as a supply liquid to the collection column, or joined in the line 15 to be recycled for the prior step as extraction water or the like.

Purification Step

The organic layer (acrylonitrile solution) containing acrylonitrile, hydrogen cyanide, and a small amount of water is supplied to the hydrocyanic acid-removing dehydration column 18 with the line 17. An aqueous hydroquinone solution may be added in the hydrocyanic acid-removing dehydration column 18. Vapor containing hydrogen cyanide is distilled out from the top of the hydrocyanic acid-removing dehydration column 18 from a line 19 and is fed to a condenser 20 to be cooled and partially condensed. A condensed hydrogen cyanide liquid is refluxed to the top with a line 22, and a crude hydrogen cyanide gas which has not been condensed and which contains small amounts of impurities is withdrawn outside the system from a line 21. If necessary, the crude hydrogen cyanide gas is purified in a distillation column not illustrated in Figures and is used as a raw material for a hydrogen cyanide derivative such as sodium cyanide. The condenser 20 is preferably vertical, and an organic acid, such as, for example, acetic acid, is preferably sprayed on an upper tube plate to suppress polymerization of hydrogen cyanide. The amount of the organic acid to be sprayed is preferably 1 to 4 kg/t-acrylonitrile based on acrylonitrile to be obtained as a product from a product column 25 described later. As a refrigerant 20a (see FIG. 2) used for the condenser 20, water or an aqueous methanol solution is used at a supply temperature of 0 to 35° C., preferably 3 to 30° C. The unit represented by kg/t-acrylonitrile means mass (kg) per 1 ton of acrylonitrile.

Distillation in the hydrocyanic acid-removing dehydration column comprises a first step of separating a side stream withdrawn from the first position of the hydrocyanic acid-removing dehydration column 18 with a line 23 into two layers of an organic layer and an aqueous layer, and then returning the organic layer to the second position of the hydrocyanic acid-removing dehydration column 18, the second position positioned below the first position.

Specifically, as illustrated in FIG. 2, a chimney tray B is provided at the first position of the hydrocyanic acid-removing dehydration column 18 to take out a liquid in the column, the liquid retained in the chimney tray, as a side stream, and the liquid is then cooled with a side cut cooler 23b and thereafter is supplied to a decanter 23d to be separated into two layers of the organic layer and the aqueous layer. The aqueous layer in the decanter is recycled with a line 23f for a prior step such as a step in the collection column 12 or the like. The organic layer in the decanter is returned to the above-described second position of the hydrocyanic acid-removing dehydration column 18 with a line 23e.

In the past, blocking of holes in a plate (tray) occurred below the chimney tray B of the hydrocyanic acid-removing dehydration column because a polymerized product is generated by continuous operation, and it was difficult to conduct continuous operation for a long period of time even though a radical polymerization inhibitor such as hydroquinone was added. In contrast, since the distillation in the hydrocyanic acid-removing dehydration column comprises the second step of supplying water through a line 23g from the third position positioned below the second position and above the lowermost stage of the hydrocyanic acid-removing dehydration column to the hydrocyanic acid-removing dehydration column 18, continuous operation for a longer period of time is made possible. The second step in the hydrocyanic acid-removing dehydration column will be described in detail later.

Heat that is necessary for distillation is supplied from a reboiler 24a through a line 24c. As a heat medium 24b, water vapor, or high-temperature process water taken out from the lower part of the column (lines 14 and 15) and/or the bottom (line 13) of the collection column 12 is preferably used. The position where the heat is supplied to the hydrocyanic acid-removing dehydration column 18 with the line 24c is preferably a lower part of the lowermost stage D.

The amount of heat given to the hydrocyanic acid-removing dehydration column 18 by the reboiler 24a is preferably $150 \times 10^3$ to $280 \times 10^3$ kcal/t-acrylonitrile, more preferably $170 \times 10^3$ to $230 \times 10^3$ kcal/t-acrylonitrile from the viewpoint of performing separation and collection of acrylonitrile in the hydrocyanic acid-removing dehydration column 18 efficiently. The mass of acrylonitrile herein is the mass (t) of acrylonitrile obtained as a product from the product column 25 described later and the above-described numerical values each represent the amount of heat per unit mass of acrylonitrile (kcal/t-acrylonitrile) and therefore can be each referred to as a "heat consumption rate".

Crude acrylonitrile is withdrawn as a bottom liquid from the bottom of the hydrocyanic acid-removing dehydration column 18 with the line 24 and is fed to the product column 25. It is to be noted that part of the bottom liquid withdrawn with the line 24 is supplied to the reboiler 24a to be heated and thereafter is returned to the hydrocyanic acid-removing dehydration column 18.

The production column 25 is a plate distillation column that is operated under a pressure lower than the atmospheric pressure. The vapor distilled out from the production column 25 is withdrawn through a line 26 and is fed to a condenser 30 to be condensed. The condensed liquid is refluxed to the product column 25 through a line 31, and part of the liquid is withdrawn through a line 29. The bottom liquid containing a high-boiling point substance is withdrawn from a line 28. In the process illustrated in FIG. 1, acrylonitrile obtained from the side stream withdrawn from a line 27 is obtained as a product.

In the process for producing acrylonitrile, the amount of acrylonitrile to be produced may be increased or decreased even during normal operation due to production planning or the like. In that case, the amount of the acrylonitrile solution to be fed to the hydrocyanic acid-removing dehydration column 18 is increased or decreased, and the necessity for adjusting operation conditions of the distillation apparatus arises.

The "distillation apparatus" according to the present embodiment may include incidental facilities of the distillation column, such as a reboiler and a condenser, in addition to the distillation column. In the distillation apparatus according to the present embodiment, a cooler that cools a side stream withdrawn from a middle stage of the distillation column and a decanter in which oil-water separation is performed are included.

FIG. 2 shows a schematic diagram schematically illustrating a distillation apparatus consisting of the hydrocyanic acid-removing dehydration column 18 and facilities connected thereto.

The hydrocyanic acid-removing dehydration column 18 is a plate distillation column that is operated under normal pressure, and the number of plates thereof is preferably 50 stages to 65 stages. The types of the plate for use include a sieve tray, a dual-flow tray, and the like, but are not limited to these. It is to be noted that the lowermost stage and the uppermost stage of a distillation column denote the position of the lowermost stage and the position of the uppermost stage of the plates in the distillation column, respectively.

A feed liquid (acrylonitrile solution containing acrylonitrile, hydrogen cyanide, and water) to the hydrocyanic acid-removing dehydration column 18 is supplied to a feed stage A from the line 17. The position of the feed stage A is above the chimney tray B and below the uppermost stage E. The position of the feed stage A is preferably 10 stages to 25 stages above the chimney tray B. When the feed liquid is supplied, vapor rises in the column, and the vapor containing hydrogen cyanide is distilled out from the top through the line 19. The vapor distilled out is fed to the condenser 20 to be cooled and partially condensed. A condensed hydrogen cyanide liquid is refluxed to the uppermost stage E of the column with the line 22, and the crude hydrogen cyanide gas which has not been condensed and which contains small amounts of impurities is withdrawn outside the system from the line 21. The reflux liquid that flows down in the column and the vapor that rises in the column come into contact with each other, and purification by distillation is performed.

The side stream is withdrawn with the line 23 from the chimney tray B that is in the middle stage of the hydrocyanic acid-removing dehydration column 18, cooled with the side cut cooler 23b by a refrigerant 23a, then supplied to the decanter 23d with the line 23c, and separated into the two layers of the organic layer and the aqueous layer in the decanter 23d. In the present embodiment, the "middle stage" denotes a part that is below the top and above the bottom, and, in the case of the multi-stage distillation column, denotes one stage between the uppermost stage E and the lowermost stage D. For example, in the case of the distillation column having a total number of stages of 50 to 65, it is preferable that the first position where the line 23 is provided be usually set at the 20th to 35th stage when the lowermost stage D is counted as the first stage from the viewpoint of separating water from crude acrylonitrile efficiently. As the refrigerant 23a, water or an aqueous methanol solution is used at a supply temperature of preferably 0 to 35° C., more preferably 3 to 30° C. The amount of heat removed at the side cut cooler 23b is adjusted with reference to a thermometer (not illustrated in Figures) for measuring the temperature of a liquid, the thermometer installed in the decanter 23d. The liquid temperature in the decanter is preferably controlled to be constant in a range from 20 to 40° C. The aqueous layer in the decanter is recycled with the line 23f for a prior step such as a step in the collection column 12 or the like. The organic layer in the decanter is returned to the second position that is a stage below the first position and above the lowermost stage D with the line 23e. The second position is preferably one stage below the first position, namely a stage immediately below the chimney tray B. The organic layer in the decanter may be preliminarily heated and then returned to the second position.

The part below the chimney tray B of the hydrocyanic acid-removing dehydration column 18 is called a dehydration part and has the function of removing most of water from the acrylonitrile solution. In the purification method according to the present embodiment, a method that is opposite to the function, namely a method of supplying water to the dehydration part, is carried out.

As described above, in the dehydration part, a polymer is generated through polymerization to block the plates (trays), thereby inhibiting the continuous operation over a long period of time, but according to studies conducted by the present inventor, it has been found from the analysis of a polymerized product that trays and the like are clogged mainly due to polymerization of acrylonitrile. It is inferred that the polymerization mechanism of acrylonitrile in the dehydration part is radical polymerization. The polymerization is not completely suppressed with hydroquinone or the like that is used as a polymerization inhibitor, so that the trays are clogged over time to increase pressure loss. The present inventor has conducted diligent studies to find that it is effective to add water in the dehydration part for the purpose of suppressing the polymerization of acrylonitrile.

In the method for purifying acrylonitrile according to the present embodiment, water is supplied to a stage C positioned at the third position that is below the second position and above the lowermost stage D of the hydrocyanic acid-removing dehydration column from the viewpoint of mainly preventing the polymerization of acrylonitrile in the dehydration part. The "below the second position" herein does not include the second position itself, and the "above the lowermost stage D" does not include the lowermost stage D itself. The position of the stage C is preferably the 0.2n-th to the 0.8n-th stage, more preferably the 0.3n-th to the 0.6n-th stage when the lowermost stage D is counted as the 1st stage; a stage that is one stage above the lowermost stage D is counted as the 2nd stage; and stages are counted one by one to assume that the chimney tray B is counted as the n-th stage. A plurality of stages C that supply water may be present.

In the case where water is supplied to the chimney tray B, water that is added from the line 23 via the decanter 23d is withdrawn to the water layer side and does not flow into the column, and therefore an effect of suppressing polymerization is not exhibited. In the case where water is supplied to the lower part of the column, including the lowermost stage D, although the water contributes to mainly preventing the polymerization of acrylonitrile, the polymerization prevention effect is remarkably lower than in the case where water is supplied to the stage C, which is the method according to the present invention.

With respect to the quality of water to be supplied, water not containing a substance that has an influence on the quality of acrylonitrile products may be used; however, water that is generally called demineralized water or pure water in chemical plants may also be used, and the quality of water is preferably the same quality as, for example, that of water which is used for boilers and in which a boiler compound is not added.

With respect to the amount of water to be supplied, the lower limit is determined from the viewpoint of suppressing the polymerization in the dehydration part. In addition, the upper limit of the amount to be supplied is determined from the viewpoint of keeping the specification of water for a product acrylonitrile obtained from the line 27. The amount of water to be supplied is preferably adjusted so that the concentration of water in the bottom liquid withdrawn from the line 24 is 0.1 to 2.0% by mass and is more preferably adjusted so that the concentration of water is 0.3 to 1.5% by mass. In the case where the amount of water to be supplied is adjusted as described above, the amount of water to be supplied is preferably 2 to 15 kg/t-acrylonitrile, more preferably 4 to 12 kg/t-acrylonitrile.

In an acrylonitrile distillation apparatus of a commercial scale, acrylonitrile is preferably used as a key material in the top of the hydrocyanic acid-removing dehydration column, and hydrogen cyanide and water are each preferably used as a key material in the bottom. When the concentration of acrylonitrile in a hydrogen cyanide gas distilled out from the top is kept low, lowering the mass of acrylonitrile obtained as a product can be prevented. In addition, hydrogen cyanide is also one of products to be sold on the market and is utilized for various hydrogen cyanide derivatives, and when the concentration of acrylonitrile in hydrogen cyanide is kept low, for example, undesirable coloration or the like of methyl methacrylate (MMA) obtained by an acetone cyanohydrin (ACH) method can be prevented. Even though acrylonitrile is distilled out from the top, the purity of hydrogen cyanide can be improved by further performing separation by distillation or the like, but, in addition to the separation facilities such as the distillation apparatus, facilities for disposing waste water containing acrylonitrile discharged from the separation facilities is also an essential requirement. Thus, the concentration of acrylonitrile distilled out from the top is preferably kept low in hydrogen cyanide in consideration of utilization of hydrogen cyanide.

Similarly, the concentrations of hydrogen cyanide and water in the bottom liquid are preferably kept at a low concentration. In the case where a large amount of hydrogen cyanide is mixed into acrylonitrile withdrawn from the bottom of the hydrocyanic acid-removing dehydration column, the hydrogen cyanide becomes a cause for coloration in an acrylic fiber or an ABS resin obtained using the acrylonitrile. The concentration of hydrogen cyanide in acrylonitrile withdrawn from the bottom is preferably 5 to 100 ppm by mass, more preferably 10 to 60 ppm by mass. In addition, in the case where a large amount of water is mixed into the bottom liquid, the purity of acrylonitrile as a product is lowered.

Changes in the concentrations of the key materials in the top and the bottom are measured by increasing or decreasing the heating amount of the reboiler. From the measurement results, the heating amount of the reboiler preferable for exhibiting a favorable performance of separation by distillation is determined. The heating amount of the reboiler is preferably $150\times10^3$ to $300\times10^3$ kcal/t-acrylonitrile, more preferably $170\times10^3$ to $280\times10^3$ kcal/t-acrylonitrile.

It can be said that adjusting the heating amount of the reboiler with reference to the concentrations of the key materials, the concentrations obtained by analysis, is preferable from the viewpoint of purifying acrylonitrile so that the specification for separating key materials can be satisfied.

In the process for producing acrylonitrile, the amount of acrylonitrile to be produced may be increased or decreased even during normal operation due to production planning or the like. In the case where the amount of acrylonitrile to be produced is increased or decreased, the amount of the solution to be fed to the hydrocyanic acid-removing dehydration column 18 is increased or decreased. In addition, the amount of water to be supplied to the column (hereinafter, referred to as "amount of water to be supplied") is adjusted and changed according to the change in the mass of the solution to be fed from viewpoint of the amount of a product to be produced and the above-described original unit of supplying water. Furthermore, similarly, the amount of heat applied to the reboiler (hereinafter, referred to as "reboiler heating amount") is adjusted and changed from the viewpoint of the above-described heat consumption rate of the reboiler.

Distillation Apparatus

The apparatus for carrying out the method for purifying acrylonitrile according to the present embodiment is not particularly limited, and examples thereof include a distillation apparatus comprising: a distillation column; a first line that takes out a side stream from a first position of the distillation column; a cooler that cools the side stream; a decanter that separates the side stream having passed through the cooler into an organic layer and an aqueous layer; a second line that returns the organic layer to a second position of the distillation column, the second position positioned below the first position; and a third line that introduces water from a third position of the distillation column, the third position positioned below the second position and above the lowermost stage of the distillation column. Examples of specific, preferred embodiments include the above-described distillation apparatus consisting of the hydrocyanic acid-removing dehydration column described in FIG. 2 and facilities connected thereto.

EXAMPLES

Hereinafter, the present embodiment will be described in more detail giving Examples; however, the present embodiment is not limited by Examples described below. It is to be noted that the acrylonitrile production process in Examples and Comparative Examples is the same as that illustrated in FIG. 1. In addition, the hydrocyanic acid-removing dehydration column in Examples is the same as that illustrated in FIG. 2.

Analysis of acrylonitrile was conducted by gas chromatography with the following apparatus under the following conditions.

In the gas chromatography, Shimadzu GC-17A was used as an apparatus, and TC-FFAP of 60 m×0.32 with a film thickness of 0.25 μm was used as a column. FID was used as a detector, and helium was used as a carrier gas.

Temperature conditions of the column were as follows.
Initial temperature: 50° C.
Temperature elevation rate: 5° C./minute
Final temperature 1: kept at 180° C. for 15 minutes
Temperature elevation rate: 10° C./minute
Final temperature 2: kept at 230° C. for 10 minutes
Final temperature 3: kept at 50° C. for 5 minutes
Analysis of hydrogen cyanide and of water were conducted by a silver nitrate titration method and by a Karl Fischer method, respectively.

The following flowmeter and thermometer were used.
Flowmeter: differential pressure flowmeter (orifice type), rotameter manufactured by YOKOGAWA, and the like
Thermometer: resistance thermometer manufactured by OKAZAKI Example 1

Propylene, ammonia, and air were supplied to a vertical cylinder type fluidized bed reactor 1 having an inner diameter of 8 m and a height of 20 m, and ammoxidation reaction of propylene was conducted as follows. The fluidized bed reactor 1 had a raw material gas dispersion tube, a dispersion plate, a heat removal tube, and a cyclone therein. The hydrocyanic acid-removing dehydration column 18 had: 55 stages of sieve trays; the feed stage A at the 37th stage counted from the bottom; the chimney tray B at the 24th stage; the line 23 that withdraws a side cut stream at the 24th stage; and, at the 23rd stage, the line 23e that returns the organic layer in the decanter via the side cut cooler 23b and the decanter 23d. The water-supplying stage C was the 10th stage counted from the bottom.

As the fluidized bed catalyst, a molybdenum-bismuth-iron-supported catalyst having a particle diameter of 10 to 100 μm and an average particle diameter of 55 μm was used and packed so that a stationary bed had a height of 2.7 m. Air was supplied from the air dispersion plate at a flow rate of 56000 Nm$^3$/h, and, from the raw material gas dispersion tube, propylene was supplied at a flow rate of 6200 Nm$^3$/h, and ammonia was supplied at a flow rate of 6600 Nm$^3$/h. The reaction temperature was controlled to be 440° C. with the heat removal tube. The pressure was 0.70 kg/cm$^2$G.

A reaction-generated gas was introduced into the quench column 6 to bring into a countercurrent contact with water, and unreacted ammonia was removed by neutralization with sulfuric acid. The gas flowed out from the quench column 6 was introduced into the absorption column 9 from the line 8. Absorption water was introduced from the line 14 at the top of the absorption column 9 to bring into a countercurrent contact with the gas to allow acrylonitrile, acetonitrile, and hydrogen cyanide in the gas to be absorbed in water. The amount of absorption water was adjusted so that the concentration of acrylonitrile in the gas discharged from the top of the absorption column was 100 vol. ppm. The gas which had not been absorbed was taken out from the line 11 at the top of the absorption column to be incinerated.

The bottom liquid in the absorption column was preliminarily heated to 80° C. and was then supplied to the collection column 12 from the line 10. In the collection column 12, acetonitrile was separated with the line 16, and most of water was separated with the line 13. Acrylonitrile, hydrogen cyanide, and water were distilled out from the line 17 at the top. The vapor distilled out was condensed with a condenser not illustrated in Figures, and an aqueous hydroquinone solution was added in the condenser so that the concentration of hydroquinone in the line 24 was 400 ppm by mass. The condensed liquid from the condenser was put into a collection column decanter not illustrated in Figures to form an organic layer and an aqueous layer, the aqueous layer was recycled to the line 10 for supplying to the collection column 12, and the organic layer was supplied to the hydrocyanic acid-removing dehydration column 18.

The mass and temperature of a feed liquid to the hydrocyanic acid-removing dehydration column 18 were measured with a flowmeter and a thermometer each installed in the line 17 and each not illustrated in Figures, and the measured values were 13595 kg/h and 35.0° C., respectively. The concentrations of acrylonitrile, hydrogen cyanide, and water in the feed liquid were 85.7% by mass, 4.7% by mass, and 9.4% by mass, respectively.

A crude hydrogen cyanide gas was withdrawn from the top line 19 of the hydrocyanic acid-removing dehydration column 18 and was then fed to the condenser 20 to be cooled and partially condensed. The refrigerant 20a used for the condenser 20 was water of 6° C. Acetic acid was sprayed on the upper tube plate in the condenser 20 in an amount of 3.0 kg/t-acrylonitrile with a spray. The condensed hydrogen cyanide liquid was refluxed to the top, and the hydrogen cyanide gas which had not been condensed and which contains small amounts of impurities was withdrawn outside the system from the line 21.

The side stream withdrawn from the chimney tray B (first position) at the 24th stage of the hydrocyanic acid-removing dehydration column 18 was cooled with the side cut cooler 23b. The refrigerant 23a used for the side cut cooler 23b was water of 6° C. The amount of heat removed with the side cut cooler was adjusted by the flow rate of the refrigerant 23a so that the liquid temperature in the decanter 23d was 25° C. The cooled side stream was separated into two layers of an organic layer and an aqueous layer in the decanter 23d, and the aqueous layer was withdrawn with the line 23f to be recycled as a supply liquid to the collection column 12. The organic layer was returned to the 23rd stage (second position) of the column with the line 23e.

As a source of heat for the reboiler 24a, process water of 110° C. withdrawn from the lower part of the collection column 12 was used. The amount of heat given was 200×10$^3$ kcal/t-acrylonitrile, and the mass of acrylonitrile obtained as a product in the product column 25 was 11.5 t per hour, and therefore the flow rate of process water 24b leading to the reboiler 24a was adjusted so that the amount of heat was 2300×10$^3$ kcal/h.

Crude acrylonitrile was withdrawn from the bottom line 24 and was then fed to the product column 25. The mass of the liquid withdrawn from the bottom was measured with a flowmeter installed in the line 24 and not illustrated in Figures to find that the measured value was 11585 kg/h. The temperature of the liquid withdrawn from the bottom was the same as the temperature of the bottom liquid in the hydrocyanic acid-removing dehydration column 18 to be 86° C. In the liquid withdrawn from the bottom, the concentration of water was 0.60% by mass, and the concentration of hydrogen cyanide was 25 ppm by mass.

Supplying water from the line 23g through a flowmeter not illustrated in Figures was started. The amount of water to be supplied was set at 8.5 kg/t-acrylonitrile to be 98 kg/h. The amount of heat of the reboiler 24a was set at 201×10$^3$ kcal/t-acrylonitrile to be 2312×10$^3$ kcal/h. In the liquid withdrawn from the bottom, the concentration of water was 0.65% by mass, and the concentration of hydrogen cyanide was 28 ppm by mass.

The operation was continued for 22 months during which the amount of acrylonitrile to be produced was set at 11.5±0.1 t/h. The hydrocyanic acid-removing dehydration column 18 was able to be operated stably, and a high-purity acrylonitrile product was able to be obtained stably.

After the operation of the hydrocyanic acid-removing dehydration column 18 was stopped, a manhole was opened to inspect trays. A white polymer was adhered thinly to the trays of the dehydration part, but the state was such that the holes of the trays were not blocked.

Example 2

Acrylonitrile was produced in the same facilities by the same method as those in Example 1 except that the amount of acrylonitrile to be produced was increased to 12.7 t/h.

The amount of water to be supplied was set at 108 kg/h, and the amount of heat of the reboiler Q1 was increased up to 2553×10$^3$ kcal/h. Respective temperatures in the hydrocyanic acid-removing dehydration column 18 and the temperature of the decanter 23d were almost the same as those in Example 1. In the liquid withdrawn from the bottom, the concentration of water was 0.66% by mass, and the concentration of hydrogen cyanide was 28 ppm by mass.

The operation was continued for 22 months during which the amount of acrylonitrile to be produced was set at 12.7±0.1 t/h. The hydrocyanic acid-removing dehydration column 18 was able to be operated stably, and a high-purity acrylonitrile product was able to be obtained stably.

After the operation of the hydrocyanic acid-removing dehydration column 18 was stopped, a manhole was opened to inspect trays. A white polymer was adhered thinly to the trays of the dehydration part, but the state was such that the holes of the trays were not blocked.

Example 3

Propane, ammonia, and air were supplied to the same fluidized bed reactor 1 as that in Example 1, and ammoxidation reaction of propane was conducted as follows.

As the fluidized bed catalyst, a molybdenum-vanadium-supported catalyst having a particle diameter of 10 to 100 μm and an average particle diameter of 55 μm was used and packed so that a stationary bed had a height of 2.2 m. Air was supplied from the air dispersion plate at a flow rate of 64500 Nm³/h, and, from the raw material gas dispersion tube, propane was supplied at a flow rate of 4300 Nm³/h, and ammonia was supplied at a flow rate of 4300 Nm³/h. The reaction temperature was controlled to be 440° C. with the heat removal tube. The pressure was 0.75 kg/cm²G.

A reaction-generated gas was introduced into the quench column 6 to bring into a countercurrent contact with water. In addition, unreacted ammonia was removed by neutralization with sulfuric acid. The gas taken out from the quench column 6 was introduced into the absorption column 9 from the line 8. Absorption water was introduced from the top line 14 to bring into a countercurrent contact with the gas to allow acrylonitrile, acetonitrile, and hydrogen cyanide in the gas to be absorbed in water. The gas which had not been absorbed was taken out from the line 11 at the top of the absorption column to be incinerated. The amount of absorption water was adjusted so that the concentration of acrylonitrile in the gas taken out from the top of the absorption column was 100 vol. ppm.

The bottom liquid in the absorption column was preliminarily heated and was then supplied to the collection column 12 from the line 10. In the collection column 12, both acetonitrile and most of water were separated, and acrylonitrile, hydrogen cyanide, and water were distilled out from the line 17 at the top. The vapor distilled out was condensed with a condenser not illustrated in Figures, and an aqueous hydroquinone solution was added in the condenser so that the concentration of hydroquinone in the line 24 was 400 ppm by mass. The condensed liquid from the condenser was put into a collection column decanter not illustrated in Figures to form an organic layer and an aqueous layer, the aqueous layer was recycled to the line 10 for supplying to the collection column 12, and the organic layer was supplied to the hydrocyanic acid-removing dehydration column 18.

The mass and temperature of a feed liquid to the hydrocyanic acid-removing dehydration column 18 were measured with a flowmeter and a thermometer each installed in the line 17 and each not illustrated in Figures, and the measured values were 6219 kg/h and 35.0° C., respectively. The concentrations of acrylonitrile, hydrogen cyanide, and water in the feed liquid were 84.0% by mass, 10.1% by mass, and 5.7% by mass, respectively.

A crude hydrogen cyanide gas was withdrawn from the top line 19 of the hydrocyanic acid-removing dehydration column 18 and was then fed to the condenser 20 to be cooled and partially condensed. The refrigerant 20a used for the condenser 20 was water of 6° C. Acetic acid was sprayed on the upper tube plate in the condenser 20 in an amount of 2.8 kg/t-acrylonitrile with a spray. The condensed hydrogen cyanide liquid was refluxed to the top, and the hydrogen cyanide gas which had not been condensed and which contains small amounts of impurities was withdrawn outside the system from the line 21.

The liquid in the column was withdrawn from the chimney tray B at the 24th stage (first position) of the hydrocyanic acid-removing dehydration column 18 and was then cooled with the side cut cooler 23b. The refrigerant 23a used for the side cut cooler 23b was water of 6° C. The amount of heat removed with the side cut cooler was adjusted by the flow rate of the refrigerant 23a so that the liquid temperature in the decanter 23d was 25° C. The side stream withdrawn from the hydrocyanic acid-removing dehydration column 18 was separated into two layers of an organic layer and an aqueous layer in the decanter 23d, and the aqueous layer was withdrawn with the line 23f to be recycled as a supply liquid to the collection column 12. The organic layer was returned to the 23rd stage (second position) of the hydrocyanic acid-removing dehydration column 18 with the line 23e.

As a source of heat for the reboiler 24a, process water of 110° C. withdrawn from the lower part of the collection column 12 was used. The amount of heat given was 250×10³ kcal/t-acrylonitrile, and the mass of acrylonitrile obtained as a product in the product column 25 was 5.22 t per hour, and therefore the flow rate of process water 24b leading to the reboiler 24a was adjusted so that the amount of heat was 1305×10³ kcal/h.

Crude acrylonitrile was withdrawn from the bottom line 24 and was then fed to the product column 25. The mass of the liquid withdrawn from the bottom was measured with a flowmeter installed in the line 24 and not illustrated in Figures to find that the measured value was 5312 kg/h. The temperature of the liquid withdrawn from the bottom was the same as the temperature of the bottom liquid in the hydrocyanic acid-removing dehydration column 18 to be 86° C. In the liquid withdrawn from the bottom, the concentration of water was 0.45% by mass, and the concentration of hydrogen cyanide was 18 ppm by mass.

Supplying water from the line 23g through a flowmeter not illustrated in Figures was started. The amount of water to be supplied was set at 11 kg/t-acrylonitrile to be 57 kg/h. In the liquid withdrawn from the bottom, the concentration of water was 0.59% by mass, and the concentration of hydrogen cyanide was 23 ppm by mass.

The operation was continued for 22 months during which the amount of acrylonitrile to be produced was set at 5.22±0.10 t/h. The hydrocyanic acid-removing dehydration column 18 was able to be operated stably, and a high-purity acrylonitrile product was able to be obtained stably.

After the operation of the hydrocyanic acid-removing dehydration column 18 was stopped, a manhole was opened to inspect trays. A white polymer was adhered thinly to the trays of the dehydration part, but the state was such that the holes of the trays were not blocked.

Comparative Example 1

Acrylonitrile was produced in the same facilities by the same method as those in Example 1 except that the line 23g that is equipment that supplies water to the dehydration part of the hydrocyanic acid-removing dehydration column was not used.

The mass and temperature of a feed liquid to the hydrocyanic acid-removing dehydration column 18 were measured with a flowmeter and a thermometer each installed in the line 17 and each not illustrated in Figures, and the measured values were 13595 kg/h and 35.0° C., respectively. The measured values were the same as those in Example 1.

As a source of heat for the reboiler 24a, process water of 110° C. withdrawn from the lower part of the collection column 12 was used. The amount of heat given was 200×10³ kcal/t-acrylonitrile, and the mass of acrylonitrile obtained as a product in the product column 25 was 11.5 t per hour, and therefore the flow rate of process water 24b leading to the reboiler 24a was adjusted so that the amount of heat was 2300×10³ kcal/h. The temperature of the liquid withdrawn from the bottom was the same as the temperature of the bottom liquid in the hydrocyanic acid-removing dehydration column 18 to be 86° C. In the liquid withdrawn from the bottom, the concentration of water was 0.60% by mass, and the concentration of hydrogen cyanide was 25 ppm by mass.

The operation was continued setting the amount of acrylonitrile to be produced at 11.5±0.1 t/h. An increase in differential pressure in the column the cause of which is considered to be clogging of the trays in the dehydration part had been observed since about 4 months after starting the operation. The operation was further continued, but an increase in differential pressure in the hydrocyanic acid-removing dehydration column and a rapid vertical motion of the bottom liquid level were observed 8 months after starting the operation. It was concluded that a flooding phenomenon occurred, and further continuation of the operation was abandoned.

After the operation of the hydrocyanic acid-removing dehydration column was stopped, a manhole was opened to inspect trays. A large amount of white polymer was adhered to the trays of the dehydration part, and particularly in the trays of the 6th to the 18th stage, 50 to 70% of all the holes were completely blocked.

Comparative Example 2

Acrylonitrile was produced in the same facilities by the same method as those in Example 1 except that the line 23g that supplies water to the hydrocyanic acid-removing dehydration column was installed at the chimney tray B.

The operation was continued setting the amount of acrylonitrile to be produced at 11.5±0.1 t/h. An increase in differential pressure in the column the cause of which is considered to be clogging of the trays in the dehydration part had been observed since about 4 months after starting the operation. The operation was further continued, but an increase in differential pressure in the hydrocyanic acid-removing dehydration column and a rapid vertical motion of the bottom liquid level were observed 8 months after starting the operation. It was concluded that a flooding phenomenon occurred, and further continuation of the operation was abandoned.

After the operation of the hydrocyanic acid-removing dehydration column was stopped, a manhole was opened to inspect trays. A large amount of white polymer was adhered to the trays of the dehydration part, and particularly in the trays of the 6th to the 18th stage, 50 to 70% of all the holes were completely blocked.

Comparative Example 3

Acrylonitrile was produced in the same facilities by the same method as those in Example 1 except that the line 23g that supplies water to the hydrocyanic acid-removing dehydration column was installed below the lowermost stage D.

The operation was continued setting the amount of acrylonitrile to be produced at 11.5±0.1 t/h. An increase in differential pressure in the column the cause of which is considered to be clogging of the trays in the dehydration part had been observed since about 7 months after starting the operation. The operation was further continued, but an increase in differential pressure in the hydrocyanic acid-removing dehydration column and a rapid vertical motion of the bottom liquid level were observed 10 months after starting the operation. It was concluded that a flooding phenomenon occurred, and further continuation of the operation was abandoned.

After the operation of the hydrocyanic acid-removing dehydration column was stopped, a manhole was opened to inspect trays. A large amount of white polymer was adhered to the trays of the dehydration part, and particularly in the trays of the 6th to the 18th stage, 30 to 70% of all the holes were completely blocked.

Comparative Example 4

Acrylonitrile was produced in the same facilities by the same method as those in Comparative Example 1 except that the trays of the hydrocyanic acid-removing dehydration column were changed from sieve trays to dual-flow trays.

The operation was continued setting the amount of acrylonitrile to be produced at 11.5±0.1 t/h. An increase in differential pressure in the column the cause of which is considered to be clogging of the trays in the dehydration part had been observed since about 11 months after starting the operation. The operation was further continued, but an increase in differential pressure in the hydrocyanic acid-removing dehydration column and a rapid vertical motion of the bottom liquid level were observed 13 months after starting the operation. When the dual-flow trays having a relatively higher effect of suppressing the occurrence of pollution than the sieve trays are used from the viewpoint of suppressing the pollution of the trays, the operation period can be extended more than the operation period in Comparative Example 1.

The present application claims priority based on Japanese Patent Application (Japanese Patent Application No. 2016-207039) filed on Oct. 21, 2016, the contents of which are hereby incorporated by reference.

INDUSTRIAL APPLICABILITY

The method according to the present invention has industrial applicability in the process for producing acrylonitrile.

REFERENCE SIGNS LIST

1 Fluidized bed reactor
2 Propylene and/or propane-supplying tube
3 Ammonia-supplying tube
4 Air (oxygen)-supplying tube
6 Quench column
5, 7, 8 Line
9 Absorption column
10, 11 Line
12 Collection column
13, 14, 15, 16, 17 Line
18 Hydrocyanic acid-removing dehydration column
19 Line
20 Hydrocyanic acid-removing dehydration column condenser 20a Refrigerant to be supplied to hydrocyanic acid-removing dehydration column condenser
21, 22 Line
23, 23c, 23e, 23f Line
23a Refrigerant to be supplied to hydrocyanic acid-removing dehydration column side cut cooler
23b Hydrocyanic acid-removing dehydration column side cut cooler
23d Hydrocyanic acid-removing dehydration column decanter
24, 24c Line
24a Hydrocyanic acid-removing dehydration column reboiler
24b Heat medium to be supplied to hydrocyanic acid-removing dehydration column reboiler
25 Product column
26, 27, 28, 29 Line
30 Product column condenser
31 Line
A Feed stage
B Chimney tray
C Water-supplying stage
D Lowermost stage (first stage)
E Uppermost stage

The invention claimed is:

1. A method for purifying acrylonitrile comprising a purification step of distilling an acrylonitrile solution comprising acrylonitrile, hydrogen cyanide, and water, wherein the purification step comprises:
    a first step of separating a side stream withdrawn from a first position of a distillation column into an organic layer and an aqueous layer, and then returning the organic layer to a second position of the distillation column, the second position being positioned below the first position; and
    a second step of supplying water from a third position of the distillation column, the third position being positioned below the second position and above a lowermost stage of the distillation column.

2. A method for producing acrylonitrile comprising:
    a reaction step of reacting: propylene and/or propane; ammonia; and oxygen in the presence of a catalyst;
    an absorption step of allowing a gas comprising generated acrylonitrile, acetonitrile, and hydrogen cyanide to be absorbed in water, thereby obtaining an aqueous solution;
    a collection step of distilling the aqueous solution to obtain an acrylonitrile solution comprising acrylonitrile, hydrogen cyanide, and water; and
    a purification step of separating hydrogen cyanide and water from the acrylonitrile solution to obtain acrylonitrile, wherein
    the method for purifying acrylonitrile according to claim 1 is used in the purification step.

3. A distillation apparatus for purifying acrylonitrile, comprising:
    a distillation column;
    a first line that takes out a side stream from a first position of the distillation column;
    a cooler that cools the side stream;
    a decanter that separates the side stream having passed through the cooler into an organic layer and an aqueous layer;
    a second line that returns the organic layer to a second position of the distillation column, the second position being positioned below the first position; and
    a third line that introduces water from a third position of the distillation column, the third position being positioned below the second position and above a lowermost stage of the distillation column.

* * * * *